United States Patent
Yeh

(10) Patent No.: US 7,320,888 B2
(45) Date of Patent: Jan. 22, 2008

(54) SUBMERGENCE-INDUCED PROTEIN-LIKE FACTORS

(76) Inventor: Chau-Ting Yeh, Liver Research Unit, Chang Gung Memorial Hospital, 199 Tung Hwa North Road, Taipei 105 (TW)

( * ) Notice: Subject to any disclaimer, the term of this patent is extended or adjusted under 35 U.S.C. 154(b) by 110 days.

(21) Appl. No.: 11/119,995

(22) Filed: May 2, 2005

(65) Prior Publication Data

US 2006/0019271 A1    Jan. 26, 2006

Related U.S. Application Data

(62) Division of application No. 10/236,723, filed on Sep. 5, 2002.

(51) Int. Cl.
*C12N 7/00* (2006.01)
*C07K 5/00* (2006.01)

(52) U.S. Cl. .................... 435/235.1; 530/350

(58) Field of Classification Search ................ None
See application file for complete search history.

(56) References Cited

OTHER PUBLICATIONS

Yeh etal. 2001, J Virology, vol. 7, p.*
Attwood, 2000, Science, vol. 290, p. 1-6.*
Baker et al. 2001, vol. 294, p. 1-7.*
Keril J. Blight, et al. *Efficient Initiation of HCV RNA Replication in Cell Culture*. Science 290:1972-1974, Dec. 8, 2000.
Masanori Ikeda, et al. *Selectable Subgenomic and Genome-Length Dicistronic RNA's Derived from an Infectious Molecular Clone of the HCV-N Strain of Hepatitis C Virus Replicate Efficiently in Cultured Huh7 Cells*. Journal of Virology, 76(6):2997-3006, Mar. 2002.
Alexander A. Kolykhalov, et al. *Transmission of Hepatitis C by Intrahepatic Inoculation with Transcribed RNA*. Science 277:570-574, Jul. 25, 1997.
V. Lohmann, et al. *Replication of Subgenomic Hepatitis C Virus RNAs in a Hepatoma Cell Line*. Science 285:110-113, Jul. 2, 1999.
Thomas Pietschmann, et al. *Characterization of Cell Lines Carrying Self-Replicating Hepatitis C Virus RNAs*. Journal of Virology 75(3):1252-1264, Feb. 2001.
Thomas Pietschmann, et al. *Persistent and Transient Replicaiton of Full-Length Hepatitis C Virus Genomes in Cell Culture*. Journal of Virology 76(8): 4008-4021, Apr. 2002.
Yasuhiko Sagawara, et al. *Enhancement of hepatitis C virus replication by Epstein-Barr virus-encoded nuclear antigen I*. The EMBO Journal 18(20):5755-5760, 1999.

* cited by examiner

*Primary Examiner*—Bruce R. Campell
*Assistant Examiner*—Agnieszka Boesen
(74) *Attorney, Agent, or Firm*—Rosenberg, Klein & Lee

(57) ABSTRACT

A pure polypeptide containing an amino acid sequence at least 80% identical to SEQ ID NO:5. The polypeptide, when expressed in a cell, increases susceptibility of the cell to hepatitis C virus infection.

1 Claim, No Drawings

SUBMERGENCE-INDUCED PROTEIN-LIKE FACTORS

RELATED APPLICATIONS

This application is a divisional and claims priority to U.S. application Ser. No. 10/236,723, filed Sep. 5, 2002, the content of which is incorporated herein by reference.

BACKGROUND

Hepatitis C virus (HCV) is a major cause of chronic hepatitis worldwide (Choo, et al. (1989) Science 244, 359-362). Chronic hepatitis C may lead to severe sequelae, such as liver cirrhosis and hepatocellular carcinoma (Tomimatsu, et al. (1993) Cancer 72, 683-688; and Tremolada, et al. (1992) J. Hepatol. 16, 273-281). Although scientists have made important progress in understanding molecular mechanisms for HCV replication, few data are available regarding essential cellular factors required for HCV replication (Blight, et al. (2000) Science 290, 1972-1974; Kolykhalov, et al. (1997) Science 277, 570-574; and Lohmann, et al. (1999) Science 285, 110-113).

SUMMARY

This invention is based on the discovery of a human hepatic factor that is capable of supporting HCV replication in an otherwise nonpermissive cell. This protein is designated "submergence-induced protein-like factor" or "Sip-L." See, e.g., GenBank Accession Number AF403478. The full-length human Sip-L cDNA (SEQ ID NO:1) is shown below:

NO:3) including nucleotides 1 to 348 of SEQ ID NO:1. The amino acid sequence encoded by ORF-1 is designated SEQ ID NO:4; the amino acid sequence encoded by ORF-2 is designated SEQ ID NO:5. "Human Sip-L protein," as used herein, refers to the polypeptide of SEQ ID NO:5 or its variant with an equivalent biological function (e.g., a fragment of SEQ ID NO:5).

Accordingly, the invention features a pure polypeptide including an amino acid sequence at least 80% (e.g., at least 85, 90, 95, or 99; or 100%) identical to SEQ ID NO:5. When expressed in a cell, the polypeptide increases susceptibility of the cell to HCV infection. The polypeptides of the invention can be used for producing Sip-L antibodies (either monoclonal or polyclonal). These antibodies in turn are useful for detecting the presence and distribution of Sip-L proteins in tissues and in cellular compartments. For example, such antibodies can be used to verify the expression of Sip-L proteins in a transgenic animal.

A "pure polypeptide" refers to a polypeptide substantially free from naturally associated molecules, i.e., it is at least 75% (e.g., at least 80, 85, 90, or 95; or 100%) pure by dry weight. Purity can be measured by any appropriate standard method, for example, by column chromatography, polyacrylamide gel electrophoresis, or HPLC analysis.

The "percent identity" of two amino acid sequences is determined using the algorithm of Karlin and Altschul ((1990) Proc. Natl. Acad. Sci. USA 87, 2264-2268), modified as in Karlin and Altschul ((1993) Proc. Natl. Acad. Sci. USA 90, 5873-5877). Such an algorithm is incorporated into the XBLAST programs of Altschul, et al. ((1990) J. Mol. Biol. 215, 403-410). BLAST protein searches are performed with the XBLAST program, score=50, wordlength=3. Where gaps exist between two sequences, Gapped BLAST is utilized as described in Altschul, et al. ((1997) Nucleic Acids Res. 25, 3389-3402). When utilizing BLAST and

```
         GGCAAC CCCACCGCCC CGACCCCGGC CGCCCAGTGG GCCTGGAGCA GCTGCGGCGG

-90 CTCGGGGTGC TCTACTGGAA GCTGGATGCT GACAAATATG AGAATGATCC AGAATTAGAA
              ORF-1 PROTEIN:  M   L    T   N   M    R   M   I    Q   N (SEQ ID NO:4)

-30 AAGATCCGAA GAGAGAGGAA CTACTCCTGG ATGGACATCA TAACCATATG CAAAGATAAA
              ORF-2 PROTEIN:  M   D   I    I   T   I   C    K   D   K                10

31 CTACCAAATT ATGAAGAAAA GATTAAGATG TTCTACGAGG AGCATTTGCA CTTGGACGAT
     L   P   N    Y   E   E   K    I   K   M    F   Y   E    E   H   L   H    L   D   D    30

90 GAGATCCGCT ACATCCTGGA TGGCAGTGGG TACTTCGATG TGAGGGACAA GGAGGACCAG
     E   I   R    Y   I   L   D    G   S   G    Y   F   D    V   R   D   K    E   D   Q    50

150 TGGATCCGA TCTTCATGGA GAAGGGAGAC ATGGTGACGC TCCCCGCGGG GATCTATCAC
     W   I   R    I   F   M   E    K   G   D    M   V   T    L   P   A   G    I   Y   H    70

210 CGCTTCACGG TGGACGAGAA GAACTACACG AAGGCCATGC GGCTGTTTGT GGGAGAACCG
     R   F   T    V   D   E   K    N   Y   T    K   A   M    R   L   F   V    G   E   P    90

270 GTGTGGACAG CGTACAACCG GCCCGCTGAC CATTTTGAAG CCCGCGGGCA GTACGTGAAA
     V   W   T    A   Y   N   R    P   A   D    H   F   E    A   R   G   Q    Y   V   K   110

330 TTTCTGGCAC AGACCGCCTA GCAGTGCTGC CTGGGAACTA ACACGTGCCT CGTAAAGGTC
     F   L   A    Q   T   A  (SEQ ID NO:5)

390 CCCAATGTAA TGACTGAGCA GAAAATCAAT CACTTTCTCT TTGCTTTTAG AGGATAGCCT

450 TGAGGCTAGA TTATCTTTCC TTTGTAAGAT TATTTGATCA GAATATTTTG TAATGAAAGG

510 ATCTAGA (SEQ ID NO:1)
```

The nucleic acid of SEQ ID NO:1 contains two open reading frames: ORF-1 (SEQ ID NO:2) including nucleotides—65 to—42 of SEQ ID NO:1, and ORF-2 (SEQ ID NO:3) including Gapped BLAST programs, the default parameters of the respective programs (e.g., XBLAST) are used. See www.ncbi.nlm.nih.gov.

The invention further features an isolated nucleic acid characterized in that it hybridizes under stringent conditions to SEQ ID NO:1, or a complementary sequence thereof, as well as a cell (in a culture or in a transgenic animal) containing a nucleic acid of the invention. Such a nucleic acid can be at least 15 (e.g., at least 30, 50, 100, 200, 500, or 1000) nucleotides in length. An example of a nucleic acid within the invention is an isolated nucleic acid (e.g., a vector) encoding a polypeptide of the invention, e.g., a nucleic acid that contains nucleotides 1 to 348 (SEQ ID NO:3), nucleotides—29 to 348 (SEQ ID NO:6), nucleotides—42 to 348 (SEQ ID NO:7), or nucleotides—146 to 348 (SEQ ID NO:8) of SEQ ID NO:1. These nucleic acids and cells can be used for producing the polypeptides of the invention, manufacturing high titer HCV, or generating a transgenic animal. For example, the nucleic acids of the invention can be used to determine whether a Sip-L MRNA is expressed in a tissue or cell. The nucleic acids can be used as primers in PCR-based detection methods, or as labeled probes in nucleic acid blots (e.g., Northern blots).

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

By hybridization under "stringent conditions" is meant hybridization at 65° C., 0.5×SSC, followed by washing at 45° C., 0.1×SSC.

In addition, the invention features a method of (1) expressing in a cell (e.g., a liver cell) a transcript, i.e., transcript I, that hybridizes under above-described stringent conditions to SEQ ID NO:1, or (2) expressing in a cell (e.g., a liver cell) a transcript, i.e., transcript II, that is complementary to transcript I. Transcript I, when expressed in a cell, can serve as an anti-sense RNA that binds to endogenous Sip-L mRNA to prevent it from being translated into a functional protein. Therefore, this method can be used in gene therapy for reducing susceptibility of a cell to HCV infection. Transcript II can encode a Sip-L protein, and when expressed in a cell, is translated into a Sip-L protein. Thus, this method can be used for producing a polypeptide of the invention.

The invention also features a method of manufacturing high titer HCV (e.g., for producing HCV vaccines). The method includes infecting a cell (e.g., a liver cell) that expresses a human Sip-L protein with HCV and allowing the virus to replicate in the cell. Production of HCV can be increased by expressing Epstein-Barr nuclear antigen-1 in the same cell.

The invention provides a method of determining susceptibility of a cell (i.e., a liver cell) to HCV infection. The method includes determining the Sip-L expression level in a cell. If the Sip-L expression level in the cell is higher than that in a normal cell, it indicates that the cell is more susceptible to HCV infection.

Further, the invention provides a method of identifying a compound for modulating susceptibility of a cell to HCV infection. The method includes contacting a compound with a cell expressing a Sip-L gene and determining the Sip-L expression level in the cell. If the Sip-L expression level in the presence of the compound is different from that in the absence of the compound, it indicates that the compound is a candidate for modulating susceptibility of a cell to HCV infection. Production of a compound thus identified is also within the scope of the invention.

The Sip-L protein has been found to be identical to the carboxyl portion of two human clones derived from ovarian cancer (GenBank Accession Number 8922762; SEQ ID NO:9) and placenta choriocarcinoma (GenBank Accession Number 12655217; SEQ ID NO:10), respectively. These two sequences have an extension of 63 additional amino acid residues at the amino terminus compared with Sip-L and only 1 amino acid (underlined below) difference between themselves. They have been designated "amino-terminus-extended form of Sip-L" or "eSip-L."

```
SEQ ID NO:9   MVLAWYMDDA PGDPRQPHRP DPGRPVGLEQ LRRLGVLYWK LDADKYENDP  50

SEQ ID NO:10  MVQAWYMDDA PGDPRQPHRP DPGRPVGLEQ LRRLGVLYWK LDADKYENDP

ELEKIRRERN YSWMDIITIC KDKLPNYEEK IKMFYEEHLH LDDEIRYILD 100

ELEKIRRERN YSWMDIITIC KDKLPNYEEK IKMEYEEHLH LDDEIRYILD

SEQ ID NO:5                         MDIITIC KDKLPNYEEK IKMFYEEHLH LDDEIRYILD

GSGYFDVRDK EDQWIRIFME KGDMVTLPAG IYHRFTVDEK NYTKAMRLFV 150

GSGYFDVRDK EDQWIRIFME KGDMVTLPAG IYHRFTVDEK NYTKAMRLFV

GSGYFDVRDK EDQWIRIFME KGDMVTLPAG IYHRFTVDEK NYTKAMRLFV

GEPVWTAYNR PADHFEARGQ YVKFLAQTA

GEPVWTAYNR PADHFEARGQ YVKFLAQTA

GEPVWTAYNR PADHFEARGQ YVKFLAQTA
``` eSip-L has been found to be expressed in liver cancer but not in normal liver tissue. It is thus useful for diagnosing and treating liver cancer.

In one aspect, this invention features a method of determining whether a subject is suffering from or at risk for developing liver cancer. The method includes providing a sample (e.g., a liver sample) from a subject and determining the eSip-L expression level in the sample. If the eSip-L expression level in the sample is higher than that in a sample from a normal subject, it indicates that the subject is suffering from or at risk for developing liver cancer. The eSip-L expression level can be determined by measuring the amount of the eSip-L mRNA or the eSip-L protein. The eSip-L mRNA level can be determined, for example, by in situ hybridization, PCR, or Northern blot analysis. The eSip-L protein level can be determined, for example, by Western blot analysis.

In another aspect, this invention features a method of identifying a compound for treating liver cancer. The method includes contacting a compound with a cell (e.g., a liver cell) and determining the eSip-L expression level in the cell. If the eSip-L expression level in the presence of the compound is lower than that in the absence of the compound, the compound is a candidate for treating liver cancer. Production of a compound thus identified is also within the scope of the invention.

In still another aspect, this invention features a method of treating liver cancer. The method includes identifying a subject suffering from or being at risk for developing liver cancer and administering to the subject a composition to decrease the eSip-L level in the subject. The composition can contain a nucleic acid encoding a transcript characterized in that it hybridizes under stringent conditions to the sense strand of the eSip-L gene. This transcript, when expressed in a cell, can serve as an anti-sense RNA that binds to endogenous eSip-L mRNA to prevent it from being translated into a functional protein. Therefore, this method can be used in gene therapy for treating liver cancer.

Also within the scope of this invention is a pharmaceutical composition for treating liver cancer. The composition can contain a pharmaceutically acceptable carrier and a nucleic acid encoding a transcript characterized in that it hybridizes under stringent conditions to the sense strand of the eSip-L gene.

The details of one or more embodiments of the invention are set forth in the accompanying description below. Other features, objects, and advantages of the invention will be apparent from the detailed description, and from the claims.

DETAILED DESCRIPTION

Although HCV E2 protein can bind to human cells by interacting with a putative viral receptor, CD81, the interaction alone is not sufficient to establish permissiveness for HCV infection. Using an Epstein-Barr virus-based extrachromosomal replication system, a human liver cDNA library has been screened and a cDNA has been identified to be capable of supporting HCV replication in an otherwise nonpermissive cell line. Unexpectedly, this cDNA encodes a protein exhibiting homology to a group of proteins derived from various evolutionarily distant species, including Oryza sativa submergence-induced protein 2A. The human protein has thus been designated "submergence-induced protein-like factor" or "Sip-L." The mRNAs encoding this factor are heterogeneous at the 5' ends and are ubiquitously expressed in multiple tissues, albeit in a very small amount. The longest mRNA contains an in-frame and upstream initiation codon and codes for a larger protein designated "amino-terminus-extended form of Sip-L" or "eSip-L." This 5'-extended form of mRNA is detectable in hepatocellular carcinoma, but not in normal liver tissue. Immunofluorescence analysis demonstrates Sip-L is distributed evenly in cells, but occasionally formed aggregations in the peri- or intra-nuclear areas.

In one aspect, the present invention features pure Sip-L polypeptides (e.g., SEQ ID NO:5), including functional Sip-L polypeptides. A "functional polypeptide" refers to a polypeptide which possesses biological activity equivalent to that of a wild-type Sip-L protein, e.g., a fragment of a wild-type Sip-L protein.

In another aspect, the invention features isolated Sip-L nucleic acids (i.e., DNA, cDNA, and RNA) characterized in that they hybridize under stringent conditions to SEQ ID NO:1, or a complementary sequence thereof. The nucleic acids of the invention include sequences that are degenerate as a result of the genetic code.

A nucleic acid of the invention can be expressed in vitro by DNA transfer into a suitable host cell by methods known in the art. For example, the nucleic acid can be inserted into a recombinant expression vector. A variety of host-expression vector systems can be utilized to express a nucleic acid of the invention. These include, but are not limited to, microorganisms such as bacteria transformed with recombinant bacteriophage DNA, plasmid DNA, or cosmid DNA expression vectors; yeast transformed with recombinant yeast expression vectors; and human cell lines infected with recombinant virus or plasmid expression vectors. Isolation and purification of recombinant polypeptides, or fragments thereof, provided by the invention, can be carried out by conventional means including preparative chromatography and immunological separations involving monoclonal or polyclonal antibodies.

The invention also features antibodies against the Sip-L polypeptide, including monoclonal antibodies and polyclonal antibodies. The term "antibody" includes intact molecules as well as fragments thereof, such as Fab, $F(ab')_2$, and Fv which are capable of binding to an epitopic determinant present in the Sip-L polypeptide. Methods of making monoclonal and polyclonal antibodies and fragments thereof are known in the art. See, for example, Harlow and Lane (1988) Antibodies: A Laboratory Manual, Cold Spring Harbor Laboratory, New York.

Expression of Sip-L in a cell increases the susceptibility of the cell to HCV infection. High titer HCV can be recovered from such a cell, especially when Epstein-Barr nuclear antigen-1 is also expressed in the cell. The high titer HCV can be used to produce HCV vaccines. A cell that expresses Sip-L can also be used to generate an animal model for treating HCV infection. On the other hand, disruption of Sip-L expression in a cell (e.g., through anti-sense gene therapy) decreases the susceptibility of the cell to HCV infection. This method is thus useful for preventing and treating HCV infection.

The Sip-L expression level can be determined at either the mRNA level or at the protein level. Methods of measuring MRNA levels in a tissue sample are known in the art. In order to measure mRNA levels, cells can be lysed and the levels of Sip-L mRNA in the lysates or in RNA purified or semi-purified from the lysates can be determined by any of a variety of methods including, without limitation, hybridization assays using detectably labeled Sip-L-specific DNA or RNA probes and quantitative or semi-quantitative RT-PCR methodologies using appropriate Sip-L-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of measuring protein levels in a tissue sample are also known in the art. Many such methods employ antibodies (e.g., monoclonal or polyclonal antibodies) that bind specifically to the Sip-L protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to lysates of cells, and others (e.g., immunohistological methods or fluorescence flow cytometry) applied to histological sections or unlysed cell suspensions. Methods of measuring the amount of label will be depend on the nature of the label and are well known in the art. Appropriate labels include, without limitation, radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The invention also provides a method for identifying and manufacturing compounds (e.g., proteins, peptides, peptidomimetics, peptoids, antibodies, or small molecules) that modulate (increase or decrease) the Sip-L gene expression level in a cell (e.g., a liver cell). Compounds thus identified can be used, e.g., for producing HCV vaccines or preventing and treating HCV infection.

The candidate compounds of the present invention can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann, et al. (1994) J. Med. Chem. 37, 2678-85; and Lam (1997) Anticancer Drug Des. 12, 145.

Examples of methods for the synthesis of molecular libraries can be found in the art, for example, in: DeWitt, et al. (1993) PNAS USA 90, 6909; Erb, et al. (1994) PNAS USA 91, 11422; Zuckermann, et al. (1994) J. Med. Chem. 37, 2678; Cho, et al. (1993) Science 261, 1303; Carrell, et al. (1994) Angew. Chem. Int. Ed. Engl. 33, 2059; Carell, et al. (1994) Angew. Chem. Int. Ed. Engl. 33, 2061; and Gallop, et al. (1994) J. Med. Chem. 37,1233.

Libraries of compounds may be presented in solution (e.g., Houghten (1992) Biotechniques 13, 412-421), or on beads (Lam (1991) Nature 354, 82-84), chips (Fodor (1993) Nature 364, 555-556), bacteria (Ladner, U.S. Pat. No. 5,223,409), spores (Ladner, U.S. Pat. No. 5,223,409), plasmids (Cull, et al. (1992) PNAS USA 89, 1865-1869), or phages (Scott and Smith (1990) Science 249, 386-390; Devlin (1990) Science 249, 404-406; Cwirla, et al. (1990) PNAS USA 87, 6378-6382; Felici (1991) J. Mol. Biol. 222, 301-310; and Ladner supra).

To identify compounds that modulate the Sip-L gene expression level in a cell, a cell (e.g., a liver cell) is contacted with a candidate compound and the expression level of the Sip-L gene is evaluated relative to that in the absence of the candidate compound. The cell can be a cell that contains the Sip-L gene yet does not naturally expresses it, a cell that naturally expresses Sip-L, or a cell that is modified to express a recombinant nucleic acid, for example, having the Sip-L promoter fused to a marker gene. The level of the Sip-L gene expression or the marker gene expression can be determined by methods described above and any other methods well known in the art. If the expression level of the Sip-L gene or the marker gene is higher in the presence of the candidate compound than that in the absence of the candidate compound, the candidate compound is identified as being useful for producing HCV vaccines. If the expression level of the Sip-L gene or the marker gene is lower in the presence of the candidate compound than that in the absence of the candidate compound, the candidate compound is identified as a potential drug for preventing and treating HCV infection.

This invention also provides a method for preventing and treating HCV infection. Subjects to be treated can be identified, for example, by determining the Sip-L gene expression level in a sample prepared from a subject by methods described above. If the Sip-L gene expression level is higher in the sample from the subject than that in a sample from a normal person, the subject is a candidate for treatment with an effective amount of compound that decreases the Sip-L level in the subject. This method can be performed alone or in conjunction with other drugs or therapy.

In one in vivo approach, a therapeutic composition (e.g., a composition containing a compound that decreases the Sip-L gene expression level in a cell is administered to the subject. Generally, the compound will be suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. For prevention and treatment of HCV infection, the compound can be delivered directly to the liver tissue.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 μg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an anti-sense Sip-L RNA can be delivered to the subject, for example, by the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al. (1995) J. Mol. Med. 73, 479). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding an anti-sense Sip-L RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., a decreased Sip-L level) in a treated subject. As is well known in the medical arts, the dosage for any one subject depends upon many factors, including the subject's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

In addition, the invention provides methods for diagnosing and treating liver cancer, and identifying therapeutic compounds for treating such a disease using eSip-L nucleic acids and polypeptides.

A diagnostic method of this invention involves comparing the eSip-L gene expression level in a sample (e.g., a liver sample) prepared from a subject with that in a sample prepared from a normal person, i.e., a person who does not suffer from liver cancer. A higher eSip-L expression level indicates that the subject is suffering from or at risk for developing liver cancer. The methods of this invention can be used on their own or in conjunction with other procedures to diagnose liver cancer in appropriate subjects. The eSip-L expression level can be determined using methods identical to those described above for Sip-L.

This invention also provides a method for identifying and manufacturing candidate compounds (e.g., proteins, peptides, peptidomimetics, peptoids, antibodies, or small molecules) that decreases the eSip-L gene expression level in a cell (e.g., a liver cell). Compounds thus identified can be used to treat liver cancer. The candidate compounds can be obtained as described above.

To identify compounds that decrease the eSip-L gene expression level in a cell, a cell (e.g., a liver cell) is contacted with a candidate compound and the expression level of the eSip-L gene is evaluated relative to that in the absence of the candidate compound. The cell can be a cell that naturally expresses eSip-L, or a cell that is modified to express a recombinant nucleic acid, for example, having the eSip-L promoter fused to a marker gene. The level of the eSip-L gene expression or the marker gene expression can be determined by methods described above and any other methods well known in the art. When the expression level of the eSip-L gene or the marker gene is lower in the presence of the candidate compound than that in the absence of the candidate compound, the candidate compound is identified as a potential drug for treating liver cancer.

This invention also provides a method for treating liver cancer. Subjects to be treated can be identified, for example, by determining the eSip-L gene expression level in a sample prepared from a subject by methods described above. If the eSip-L gene expression level is higher in the sample from the subject than that in a sample from a normal person, the subject is a candidate for treatment with an effective amount of a compound that decreases the eSip-L level in the subject. This method can be performed alone or in conjunction with other drugs or therapy, similarly to that described above for Sip-L.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

1. Cell Lines, Transfection, and Establishment of Transformants

Human embryonic kidney cells constitutively expressing Epstein-Barr virus nuclear antigen-1 (EBNA-1) protein from Epstein-Barr virus (293EBNA cells; Invitrogen, Carlsbad, Calif.) were maintained in Dulbecco's modified Eagle's medium containing 10% fetal bovine serum and 250 µg of G418 per ml. HepG2 cells were maintained in minimal essential medium containing 10% fetal bovine serum. Huh-7 cells were maintained in Dulbecco's modified Eagle's medium containing 10% fetal bovine serum. A human liver cDNA library (Clontech Laboratories, Inc., Palo Alto, Calif.) was constructed by inserting the cDNAs into a vector, pDR2, downstream of a Rous sarcoma virus long terminal repeat (LTR) promoter. This plasmid contains Epstein-Barr virus OriP, a gene for hygromycin B selection, and an ampicillin resistance gene. The cDNA clones were first grouped into 200 sets with 100 to 200 cDNA clones per set. Plasmids were then extracted from each set of clones and transfected into 293EBNA cells by the standard $CaPO_4$ precipitation method. Transformants were selected by addition of 150 µg of hygromycin B per ml to the culture medium. A total of 200 transformants were established for the first round of the HCV infection assay.

2. HCV Infection Assay and Detection of CD81 mRNA

HCV-positive serum containing $10^7$ copies of HCV RNA per ml, measured by the branched DNA (bDNA) method (Quantiplex HCV-RNA 2.0 assay; Chiron, Emeryville, Calif.), was used for the HCV infection assay. The cells in a 60-mm-diameter petri dish were incubated in medium containing 5 µl of HCV-positive serum for 12 h. The cells were then incubated in fresh medium without HCV-positive serum, and the medium was changed every day. To detect HCV RNA, cells were trypsinized and washed two times with fresh medium by centrifugation. The supernatant of the second wash (as a contamination control) and the washed cells were collected in pairs for RNA extraction and reverse transcription (RT)-PCR. The procedures were described previously (Yeh, et al. (1997) J. Gen. Virol. 78, 2761-2770). The nested primers used were C1 (5'-CGGCAACAGG-TAAACTCCAC-3'), C2 (5'-CCCTGTGAGGAACTACT-GTC-3'), C3 (5'-ACGATCTGACCACCGCCCGG-3'), and C4 (5'-TTCACGCAGAAAGCGTCTAG-3'). A digoxigenin-labeled probe, flanking by C3 and C4, was used for the subsequent Southern blot analysis. As a control, β-actin mRNAs were detected simultaneously. The primers used were A1 (5'-CACCAACTGGGACGACATGG-3'); A2 (5'-AGGATCTTCATGAGGTAGTC-3'A3 (5'-TCTGGCAC-CACACCTTCTAC-3'), and A4 (5'-GTCAGGTCCCGGC-CAGCCAG-3'). The procedure for minus-strand-specific RT-PCR was also described previously (Yeh, et al. (1996) Biochem. Biophys. Res. Commun. 227, 524-529; and Yeh, et al. (1997) J. Gen. Virol. 78, 2761-2770). To detect CD81 mRNA, RT was performed with random primers. The primers used for PCR were 5'-CGAGACGCTTGACTGCTGTG-3' and 5'-CTCAGTACACGGAGCTGTTC-3'. The PCR product was verified by nucleotide sequencing with an automatic DNA sequencer (CEQ 2000; Beckman Instruments, Inc., Fullerton, Calif.).

3. RACE

The 5' rapid amplification of cDNA ends (RACE) experiment was performed with a 5'/3' RACE kit (Boehringer Mannheim Biochemica, Mannheim, Germany). Total normal liver RNA was used. The primer used for cDNA synthesis was PsipR (5'-CATGAAGATCCGGATCCAC-3'). After being tailed with dATP homopolymer by a terminal deoxynucleotidyl transferase, the tailed cDNA was amplified by PCR with an oligo(dT) anchor primer and P2 (5'-TCCTCCTTGTCCCTCACATC-3'). Finally, a second step of PCR was performed with an anchor primer and P4 (5'-GGATCTCATCGTCCAAGTGC-3'). The details of the experimental procedure and the sequences of oligo(dT) and the anchor primer were described previously (Yeh, et al. (1997) J. Gen. Virol. 78, 2761-2770). The sequences of clones generated by RACE (61.31R1 to 61.31R4) and two artificially created deletion mutants (61.31D1 and 61.31D2) were verified and then inserted into the BamHI-XbaI sites of pDR2 for further transfection. The restriction enzyme sites needed for plasmid construction were generated by PCR-based site-directed mutagenesis (Yeh, et al. (2000) Hepatology 31, 1318-1326). Briefly, for insertion of 61.31R1 to 61.31R4 into pDR2, two primers containing engineered BamHI and XbaI sites and complementary to the 5' and 3' ends of these clones were designed for amplification. The amplified products were digested with BamHI and XbaI, gel purified, and inserted into pDR2. For generation of the deletion mutants, the downstream primer containing the engineered XbaI site was designed to match the desired positions in 61.31R4 so that the amplified products became truncated in the 3' portion.

4. Detection of Sip-L and eSip-L mRNA

RT was performed with random primers. Sip-L mRNA was detected with P2 and P1 (5'-GGTGCTCTACTG-GAAGCTGG-3'). eSip-L mRNA was detected with P4 and P3 (5'-CCGCACTGCGCGTCATGGTG-3'). A digoxigenin-labeled probe, flanked by P1 and P2, was used for the subsequent Southern blot analysis. As a control, β-actin mRNA was also detected simultaneously.

5. Immunofluorescence Analysis

To perform immunofluorescence analysis, the coding region from clone 61.31 was isolated and inserted in frame with the V5 epitope in pcDNA3.1/V5-His B (Invitrogen, San Diego, Calif.). The plasmid was transfected into 293EBNA cells. The methods of cell fixation and staining were described previously (Yeh, et al. (1990) J. Virol. 64, 6141-6147). The primary antibody used was mouse anti-V5 monoclonal antibody (Invitrogen). The secondary antibody used was fluorescein isothiocyanate-conjugated goat anti-mouse antibody (Jackson ImmunoResearch Laboratories, Inc., West Grove, Pa.).

6. Establishment of a Stable Huh-7 Cell Line Expressing Sip-L

To establish a stable Huh-7 cell line expressing a high level of Sip-L protein, pSV2neo, which encoded a neomycin-resistant marker, and pCMVEBNA, which encodes EBNA-1 (both from Clontech), were cotransfected into Huh-7 cells. After selection with neomycin, the stable transformant was subsequently transfected with pDR2-61.31R3 and selected with hygromycin B. The stable transformant expressing the highest level of Sip-L mRNA (by Northern analysis) was used for further experimentation.

Results

1. Experimental Strategy

Expression of Epstein-Barr nuclear antigen-1 (EBNA-1) in cells allows extrachromosomal replication of plasmids carrying the Epstein-Barr virus replication origin region (OriP) (Hung, et al. (2001) Proc. Natl. Acad. Sci. USA 98, 1865-1870; Margolskee, et al. (1988) Mol. Cell. Biol. 8, 2837-2847). A cDNA library constructed with this system theoretically expresses a high level of transcripts in EBNA-1-expressing cells. Previous reports showed that HCV could infect HepG2 cells and that the viral RNA could be detected transiently (Seipp, et al. (1997) J. Gen. Virol. 78, 2467-2476). Additionally, HCV replication in the culture cells could be enhanced by expression of EBNA-1 (Sugawara, et al. (1999) EMBO J. 18, 5755-5760). Based on these observations, RT followed by a two-step (nested) PCR was performed serially after inoculation of HepG2 cells with HCV-positive serum. HCV RNA could be detected by Southern blotting, and the signal was strongest on the 8th day after inoculation. The same procedure was repeated with a human embryonic kidney cell line expressing EBNA-1 (293EBNA cells). No HCV RNA signal could be detected. However, CD81 mRNA was readily detected in 293EBNA cells. To search for the missing factor, a liver cDNA library equipped with the aforementioned Epstein-Barr virus-based system was first grouped into 200 sets with 100 to 200 clones per set. Two hundred sets of 293EBNA transformants, each transfected by one set of mixed cDNA clones, were then established. The HCV infection assay was performed with all 200 transformants to look for the positive set. Once the positive set was identified, the cDNA clones of that set were further subgrouped, and the assay was repeated until a single cDNA clone was obtained.

2. Identification of a cDNA Clone Capable of Supporting HCV Replication in 293EBNA Cells Two sets of transformants, sets 61 and 191, containing mixed cDNA clones were first identified as positive by the HCV infection assay. After subgrouping and repeating the assays, two cDNA clones from set 61 and one cDNA clone from set 191 were tested as positive by the HCV infection assay. Nucleotide sequence analysis revealed that all three clones were identical. Clone 61.31 (containing nucleotides—29 to 517 of SEQ ID NO:1) and the corresponding transformant were used for further experiments. In this extrachromosomal replication system, the plasmid containing the cDNA fragment was selected and maintained with hygromycin B. The 61.31 293EBNA cells were then cultured in medium without hygromycin B to allow for the loss of the extrachromosomal plasmid DNA (Hambor, et al. (1988) Proc. Natl. Acad. Sci. USA 85, 4010-4014). The HCV infection assay was performed serially 1 to 7 weeks after removal of hygromycin B. Cell susceptibility to HCV infection was gradually lost, and the cells became nonpermissive again 3 weeks later. To further verify the results, an HCV infection assay was performed with 61.31 293EBNA cells, and serial cell extracts were sent for HCV RNA testing performed by a molecular medicine team that routinely performs HCV RNA testing for clinical doctors using a standard assay (COBAS Amplicor HCV-RNA test). Intracellular HCV RNA was positive on days 6 and 8 after inoculation with HCV-positive serum. Finally, to confirm the presence of HCV replication in 61.31 293EBNA cells, minus-strand HCV RNA was detected 8 days after inoculation with HCV-positive serum. The result showed that minus-strand HCV RNA was indeed present in the infected cells.

3. Determination of the 5' End of Sip-L mRNA by RACE

Four different 5' ends of Sip-L mRNA were detected in total normal liver RNA by the RACE method. These clones were named 61.31R1 to 61.31R4. 61.31R1 contains nucleotides 68 to 517 of SEQ ID NO:1, 61.31R2 contains nucleotides 36 to 517 of SEQ ID NO:1, 61.31R3 contains nucleotides—42 to 517 of SEQ ID NO:1, and 61.31R4 contains nucleotides—146 to 517 of SEQ ID NO:1. Further RACE experiments with a primer located near the 5' end of 61.31R4 failed to obtain other clones. The 61.31R4 clone contained two open reading frames, ORF-1 (short, upstream) and ORF-2 (long, downstream). To determine which open reading frame is functional, all four clones obtained from RACE and two artificially deleted mutant clones (61.31D1 containing nucleotides -146 to 128 of SEQ ID NO:1 and 61.31D2 containing nucleotides—146 to—29 of SEQ ID NO:1) were transfected into 293EBNA cells to test for HCV infectivity by the same method. Preservation of ORF-2 was found to be required for HCV infectivity.

4. Clone 61.31 Encodes a Protein Factor Exhibiting Homology to Oryza Sativa Submergence-induced Protein 2A The amino acid sequence of 61.31R4 ORF-2 was compared with existing protein sequences by a BLAST search (National Center for Biotechnology Information [www.ncbi.nlm.nih.gov]). Strikingly, this protein exhibits homology to several proteins derived from various genetically distant species, including Oryza sativa submergence-induced protein 2A. The amino acid sequence of 61.31R4 ORF-2, named "submergence-induced protein-like factor" (Sip-L), was identical to the carboxyl portion of two human clones derived from ovarian cancer (GenBank Accession Number 8922762) and placenta choriocarcinoma (GenBank Accession Number 12655217), respectively. These two sequences, recently deposited in GenBank without formal publication, have an extension of 63 additional amino acid residues at the amino terminus compared with Sip-L. Only 1 amino acid difference was found between the two. They were named the "amino-terminus-extended form of Sip-L" (eSip-L).

5. Tissue Distribution of Sip-L mRNA

To determine the tissue distribution of Sip-L mRNA, Northern analysis was performed with total RNA obtained from various human organs. This experiment, however, failed to detect any Sip-L mRNA. Thus, RT followed by one-step PCR and Southern analysis was performed. Two sets of primers were designed to detect Sip-L and eSip-L mRNAs. The results indicated that Sip-L mRNA was ubiquitously distributed in all kinds of tissues, but eSip-L mRNA was found only in skeletal muscle. Strikingly, eSip-L mRNA was also detected in two samples derived from hepatocellular carcinoma.

6. Subcellular Localization of Sip-L protein in 293EBNA Cells

To gather clues for the possible physiological function of Sip-L, the subcellular localization of Sip-L was examined by immunofluorescence analysis. Sip-L was tagged with a paramyxovirus SV5 epitope for detection with anti-V5 antibody. It was found that this protein is distributed evenly in both cytoplasm and nucleus in the majority of cells. In 60% of cells, various numbers and sizes of Sip-L protein aggregations were found in either the peri- or intranuclear areas. In a few cells, the protein was heavily clustered in the nucleus.

7. Infectivity of HCV in Huh-7 Cells Stably Expressing Sip-L

The presence of Sip-L mRNA was determined in 293EBNA cells, HepG2 cells, Huh-7 cells, and normal liver tissue by RT-PCR. The amount of Sip-L mRNA in HepG2 cells was relatively smaller than that in normal liver tissue. Only a trace of Sip-L mRNA was found in Huh-7 cells. No Sip-L mRNA was detected in 293EBNA cells. An Huh-7 cell line stably expressing a high level of Sip-L mRNA was thus established (see Materials and Methods). It was found that this higher-expression line was permissive for HCV infection. Furthermore, addition of 5,000 U of α-interferon (Schering-Plough Corp., Kenilworth, N.J.) per ml to the medium from the 4th day of the infection assay resulted in a significant decrease in intracellular HCV RNA on the 7th day. Similar results were observed in 293EBNA cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of producing hepatitis C viruses, the method comprising infecting a human embryonic kidney cell line 293 expressing an Espstein-Barr nuclear antigen-1 gene and containing and expressing a nucleic acid encoding a polypeptide having SEQ ID NO:5, with a hepatitis C virus and allowing the virus to replicate in the said kidney cell line, wherein the polypeptide, when expressed in the said kidney cell line, increases susceptibility of the said kidney cell line to hepatitis C virus infection.

* * * * *

SEQUENCE LISTING

<160> NUMBER OF SEQ ID NOS: 25

<210> SEQ ID NO 1
<211> LENGTH: 663
<212> TYPE: DNA
<213> ORGANISM: Homo sapiens

```
<220> FEATURE:
<221> NAME/KEY: CDS
<222> LOCATION: (82)...(111)
<220> FEATURE:
<221> NAME/KEY: CDS
<222> LOCATION: (147)...(494)

<400> SEQUENCE: 1
ggcaacccca ccgccccgac cccggccgcc cagtgggcct ggagcagctg cggcggctcg      60
gggtgctcta ctggaagctg g atg ctg aca aat atg aga atg atc cag aat      111
                        Met Leu Thr Asn Met Arg Met Ile Gln Asn
                         1               5                  10 tagaaaagat ccgaagagag aggaactact cctgg atg gac atc ata acc ata         164
                                       Met Asp Ile Ile Thr Ile
                                                          15 tgc aaa gat aaa cta cca aat tat gaa gaa aag att aag atg ttc tac        212
Cys Lys Asp Lys Leu Pro Asn Tyr Glu Glu Lys Ile Lys Met Phe Tyr
             20              25                  30 gag gag cat ttg cac ttg gac gat gag atc cgc tac atc ctg gat ggc        260
Glu Glu His Leu His Leu Asp Asp Glu Ile Arg Tyr Ile Leu Asp Gly
             35              40                  45 agt ggg tac ttc gat gtg agg gac aag gag gac cag tgg atc cgg atc        308
Ser Gly Tyr Phe Asp Val Arg Asp Lys Glu Asp Gln Trp Ile Arg Ile
 50              55                  60 ttc atg gag aag gga gac atg gtg acg ctc ccc gcg ggg atc tat cac        356
Phe Met Glu Lys Gly Asp Met Val Thr Leu Pro Ala Gly Ile Tyr His
 65              70                  75                  80 cgc ttc acg gtg gac gag aag aac tac acg aag gcc atg cgg ctg ttt        404
Arg Phe Thr Val Asp Glu Lys Asn Tyr Thr Lys Ala Met Arg Leu Phe
                 85                  90                  95 gtg gga gaa ccg gtg tgg aca gcg tac aac cgg ccc gct gac cat ttt        452
Val Gly Glu Pro Val Trp Thr Ala Tyr Asn Arg Pro Ala Asp His Phe
             100                 105                 110 gaa gcc cgc ggg cag tac gtg aaa ttt ctg gca cag acc gcc                494
Glu Ala Arg Gly Gln Tyr Val Lys Phe Leu Ala Gln Thr Ala
             115                 120                 125 tagcagtgct gcctgggaac taacacgtgc ctcgtaaagg tccccaatgt aatgactgag      554
cagaaaatca atcactttct ctttgctttt agaggatagc cttgaggcta gattatcttt      614
cctttgtaag attatttgat cagaatattt tgtaatgaaa ggatctaga                  663

<210> SEQ ID NO 2
<211> LENGTH: 30
<212> TYPE: DNA
<213> ORGANISM: Homo sapiens

<400> SEQUENCE: 2
atgctgacaa atatgagaat gatccagaat                                        30

<210> SEQ ID NO 3
<211> LENGTH: 348
<212> TYPE: DNA
<213> ORGANISM: Homo sapiens

<400> SEQUENCE: 3
atggacatca taaccatatg caaagataaa ctaccaaatt atgaagaaaa gattaagatg       60
ttctacgagg agcatttgca cttggacgat gagatccgct acatcctgga tggcagtggg     120
tacttcgatg tgagggacaa ggaggaccag tggatccgga tcttcatgga agggagac       180 atggtgacgc tccccgcggg gatctatcac cgcttcacgg tggacgagaa gaactacacg     240
```

```
aaggccatgc ggctgtttgt gggagaaccg gtgtggacag cgtacaaccg gcccgctgac    300
cattttgaag cccgcgggca gtacgtgaaa tttctggcac agaccgcc                 348
```

<210> SEQ ID NO 4
<211> LENGTH: 10
<212> TYPE: PRT
<213> ORGANISM: Homo sapiens

<400> SEQUENCE: 4

Met Leu Thr Asn Met Arg Met Ile Gln Asn
1               5                   10

<210> SEQ ID NO 5
<211> LENGTH: 116
<212> TYPE: PRT
<213> ORGANISM: Homo sapiens

<400> SEQUENCE: 5

Met Asp Ile Ile Thr Ile Cys Lys Asp Lys Leu Pro Asn Tyr Glu Glu
1               5                   10                  15

Lys Ile Lys Met Phe Tyr Glu Glu His Leu His Leu Asp Asp Glu Ile
            20                  25                  30

Arg Tyr Ile Leu Asp Gly Ser Gly Tyr Phe Asp Val Arg Asp Lys Glu
        35                  40                  45

Asp Gln Trp Ile Arg Ile Phe Met Glu Lys Gly Asp Met Val Thr Leu
    50                  55                  60

Pro Ala Gly Ile Tyr His Arg Phe Thr Val Asp Glu Lys Asn Tyr Thr
65                  70                  75                  80

Lys Ala Met Arg Leu Phe Val Gly Glu Pro Val Trp Thr Ala Tyr Asn
                85                  90                  95

Arg Pro Ala Asp His Phe Glu Ala Arg Gly Gln Tyr Val Lys Phe Leu
            100                 105                 110

Ala Gln Thr Ala
        115

<210> SEQ ID NO 6
<211> LENGTH: 377
<212> TYPE: DNA
<213> ORGANISM: Homo sapiens

<400> SEQUENCE: 6

```
agatccgaag agagaggaac tactcctgga tggacatcat aaccatatgc aaagataaac    60
taccaaatta tgaagaaaag attaagatgt tctacgagga gcatttgcac ttggacgatg    120
agatccgcta catcctggat ggcagtgggt acttcgatgt gagggacaag gaggaccagt    180
ggatccggat cttcatggag aagggagaca tggtgacgct ccccgcgggg atctatcacc    240
gcttcacggt ggacgagaag aactacacga aggccatgcg gctgtttgtg ggagaaccgg    300
tgtggacagc gtacaaccgg cccgctgacc attttgaagc ccgcgggcag tacgtgaaat    360
ttctggcaca gaccgcc                                                    377
```

<210> SEQ ID NO 7
<211> LENGTH: 390
<212> TYPE: DNA
<213> ORGANISM: Homo sapiens

<400> SEQUENCE: 7

```
ccagaattag aaaagatccg aagagagagg aactactcct ggatggacat cataaccata    60
```

```
tgcaaagata aactaccaaa ttatgaagaa aagattaaga tgttctacga ggagcatttg      120
cacttggacg atgagatccg ctacatcctg gatggcagtg ggtacttcga tgtgagggac      180
aaggaggacc agtggatccg gatcttcatg gagaagggag acatggtgac gctccccgcg      240
gggatctatc accgcttcac ggtggacgag aagaactaca cgaaggccat gcggctgttt      300
gtgggagaac cggtgtggac agcgtacaac cggcccgctg accattttga agcccgcggg      360
cagtacgtga aatttctggc acagaccgcc                                        390

<210> SEQ ID NO 8
<211> LENGTH: 494
<212> TYPE: DNA
<213> ORGANISM: Homo sapiens

<400> SEQUENCE: 8 ggcaaccca ccgccccgac cccggccgcc cagtgggcct ggagcagctg cggcggctcg       60
gggtgctcta ctggaagctg gatgctgaca aatatgagaa tgatccagaa ttagaaaaga     120
tccgaagaga gaggaactac tcctggatgg acatcataac catatgcaaa gataaactac     180
caaattatga agaaaagatt aagatgttct acgaggagca tttgcacttg gacgatgaga     240
tccgctacat cctggatggc agtgggtact cgatgtgag ggacaaggag gaccagtgga     300
tccggatctt catggagaag ggagacatgg tgacgctccc cgcggggatc tatcaccgct     360
tcacggtgga cgagaagaac tacacgaagg ccatgcggct gtttgtggga gaaccggtgt     420
ggacagcgta caaccggccc gctgaccatt ttgaagcccg cgggcagtac gtgaaatttc     480
tggcacagac cgcc                                                        494

<210> SEQ ID NO 9
<211> LENGTH: 179
<212> TYPE: PRT
<213> ORGANISM: Homo sapiens

<400> SEQUENCE: 9

Met Val Leu Ala Trp Tyr Met Asp Asp Ala Pro Gly Asp Pro Arg Gln
  1               5                  10                  15

Pro His Arg Pro Asp Pro Gly Arg Pro Val Gly Leu Glu Gln Leu Arg
                 20                  25                  30

Arg Leu Gly Val Leu Tyr Trp Lys Leu Asp Ala Asp Lys Tyr Glu Asn
             35                  40                  45

Asp Pro Glu Leu Glu Lys Ile Arg Arg Glu Arg Asn Tyr Ser Trp Met
 50                  55                  60

Asp Ile Ile Thr Ile Cys Lys Asp Lys Leu Pro Asn Tyr Glu Glu Lys
 65                  70                  75                  80

Ile Lys Met Phe Tyr Glu Glu His Leu His Leu Asp Asp Glu Ile Arg
                 85                  90                  95

Tyr Ile Leu Asp Gly Ser Gly Tyr Phe Asp Val Arg Asp Lys Glu Asp
            100                 105                 110

Gln Trp Ile Arg Ile Phe Met Glu Lys Gly Asp Met Val Thr Leu Pro
            115                 120                 125

Ala Gly Ile Tyr His Arg Phe Thr Val Asp Glu Lys Asn Tyr Thr Lys
        130                 135                 140

Ala Met Arg Leu Phe Val Gly Glu Pro Val Trp Thr Ala Tyr Asn Arg
145                 150                 155                 160

Pro Ala Asp His Phe Glu Ala Arg Gly Gln Tyr Val Lys Phe Leu Ala
                165                 170                 175
```

Gln Thr Ala

<210> SEQ ID NO 10
<211> LENGTH: 179
<212> TYPE: PRT
<213> ORGANISM: Homo sapiens

<400> SEQUENCE: 10

Met Val Gln Ala Trp Tyr Met Asp Asp Ala Pro Gly Asp Pro Arg Gln
 1               5                  10                  15

Pro His Arg Pro Asp Pro Gly Arg Pro Val Gly Leu Glu Gln Leu Arg
            20                  25                  30

Arg Leu Gly Val Leu Tyr Trp Lys Leu Asp Ala Asp Lys Tyr Glu Asn
        35                  40                  45

Asp Pro Glu Leu Glu Lys Ile Arg Arg Glu Arg Asn Tyr Ser Trp Met
50                  55                  60

Asp Ile Ile Thr Ile Cys Lys Asp Lys Leu Pro Asn Tyr Glu Lys
65                  70                  75                  80

Ile Lys Met Phe Tyr Glu Glu His Leu His Leu Asp Asp Glu Ile Arg
                85                  90                  95

Tyr Ile Leu Asp Gly Ser Gly Tyr Phe Asp Val Arg Asp Lys Glu Asp
            100                 105                 110

Gln Trp Ile Arg Ile Phe Met Glu Lys Gly Asp Met Val Thr Leu Pro
        115                 120                 125

Ala Gly Ile Tyr His Arg Phe Thr Val Asp Lys Asn Tyr Thr Lys
    130                 135                 140

Ala Met Arg Leu Phe Val Gly Glu Pro Val Trp Thr Ala Tyr Asn Arg
145                 150                 155                 160

Pro Ala Asp His Phe Glu Ala Arg Gly Gln Tyr Val Lys Phe Leu Ala
                165                 170                 175

Gln Thr Ala

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cggcaacagg taaactccac          20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ccctgtgagg aactactgtc          20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
acgatctgac caccgcccgg                                            20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ttcacgcaga aagcgtctag                                            20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
caccaactgg gacgacatgg                                            20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aggatcttca tgaggtagtc                                            20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tctggcacca caccttctac                                            20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gtcaggtccc ggccagccag                                            20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cgagacgctt gactgctgtg                                            20

<210> SEQ ID NO 20
<211> LENGTH: 20
<212> TYPE: DNA
<213> ORGANISM: Artificial Sequence

```
<220> FEATURE:
<223> OTHER INFORMATION: Primer

<400> SEQUENCE: 20
ctcagtacac ggagctgttc                                              20

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
catgaagatc cggatccac                                               19

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tcctccttgt ccctcacatc                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ggatctcatc gtccaagtgc                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ggtgctctac tggaagctgg                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ccgcactgcg cgtcatggtg                                              20
```